United States Patent [19]

Kersten et al.

[11] Patent Number: 4,517,090
[45] Date of Patent: May 14, 1985

[54] LOW VOLUME, LARGE AREA FILTERS FOR IV OR BLOOD FILTRATION

[75] Inventors: Jean Kersten, Villers St. Amand; Jean M. Mathias, Loupoigne, both of Belgium

[73] Assignee: Baxter Travenol Laboratories, Inc., Deerfield, Ill.

[21] Appl. No.: 597,564

[22] Filed: Apr. 6, 1984

Related U.S. Application Data

[63] Continuation of Ser. No. 363,632, Mar. 30, 1982, abandoned.

[51] Int. Cl.³ .................... B01D 27/04; B01D 29/16
[52] U.S. Cl. ................. 210/493.2; 210/497.01; 210/927; 249/160; 604/4; 264/250; 264/257
[58] Field of Search ............. 210/446, 493.1, 493.2, 210/493.5, 497.01, 436, 927; 604/4, 5, 6, 405, 406; 264/250, 251, DIG. 48, 259, 271.1, 279, 275, 257, 258, 263, 267; 425/110, 117, 127, 129 R; 249/83, 117, 122, 142, 160

[56] References Cited

U.S. PATENT DOCUMENTS

| | | | |
|---|---|---|---|
| 2,489,966 | 11/1949 | Laure et al. | 210/164 |
| 3,200,953 | 8/1965 | Komarmy | 210/493.1 |
| 3,486,626 | 12/1969 | Close | 210/493.1 |
| 3,631,654 | 1/1972 | Riely et al. | 210/500 |
| 3,746,595 | 7/1973 | Leason | 264/251 |
| 3,951,145 | 4/1976 | Smith | 128/214 C |
| 3,954,623 | 5/1976 | Hammer et al. | 128/214 C |
| 4,013,072 | 3/1977 | Jess | 128/214 C |
| 4,073,732 | 2/1978 | Lauer et al. | 210/491 |
| 4,130,622 | 12/1978 | Pawlak | 264/250 |

FOREIGN PATENT DOCUMENTS 3145320  5/1983  Fed. Rep. of Germany.
113371  10/1978  Japan .................... 264/DIG. 48

OTHER PUBLICATIONS

"Blood Administration Sets", Copyrighted 1979, Travenol Laboratories, Inc.

Primary Examiner—Richard V. Fisher
Assistant Examiner—Wanda L. Millard
Attorney, Agent, or Firm—Paul C. Flattery; Gerald S. Geren; Bradford R. L. Price

[57] ABSTRACT

There is disclosed herein a flow-through medical filter element which includes surface or depth filter media and a frame-like structure for supporting and positioning the media. The frame-like structure is a molded member which includes a ring-like inlet, a fluid-impervious terminal end spaced from the inlet and a plurality of rib-like members which extend between and interconnect the inlet end and terminal end. The inlet end includes internally-extending pleat-supporting projections and the terminal end has complementary externally-extending pleat-supporting shoulders. The frame-like structure is symmetrical about an axial plane which includes the mold parting line. The external shoulders are formed at angles which permits separation of a mold along the parting line and release of the part. The filter media also includes longitudinal pleats and is secured at its ends to the pleat-supporting projections associated with the inlet end and to the external pleat-supporting shoulders at the terminal end. Thus blood enters the filter element flows through the media and thereafter exits the filter element.

This construction permits for a molding operation and provides a high surface area filter for use in existing units.

17 Claims, 9 Drawing Figures

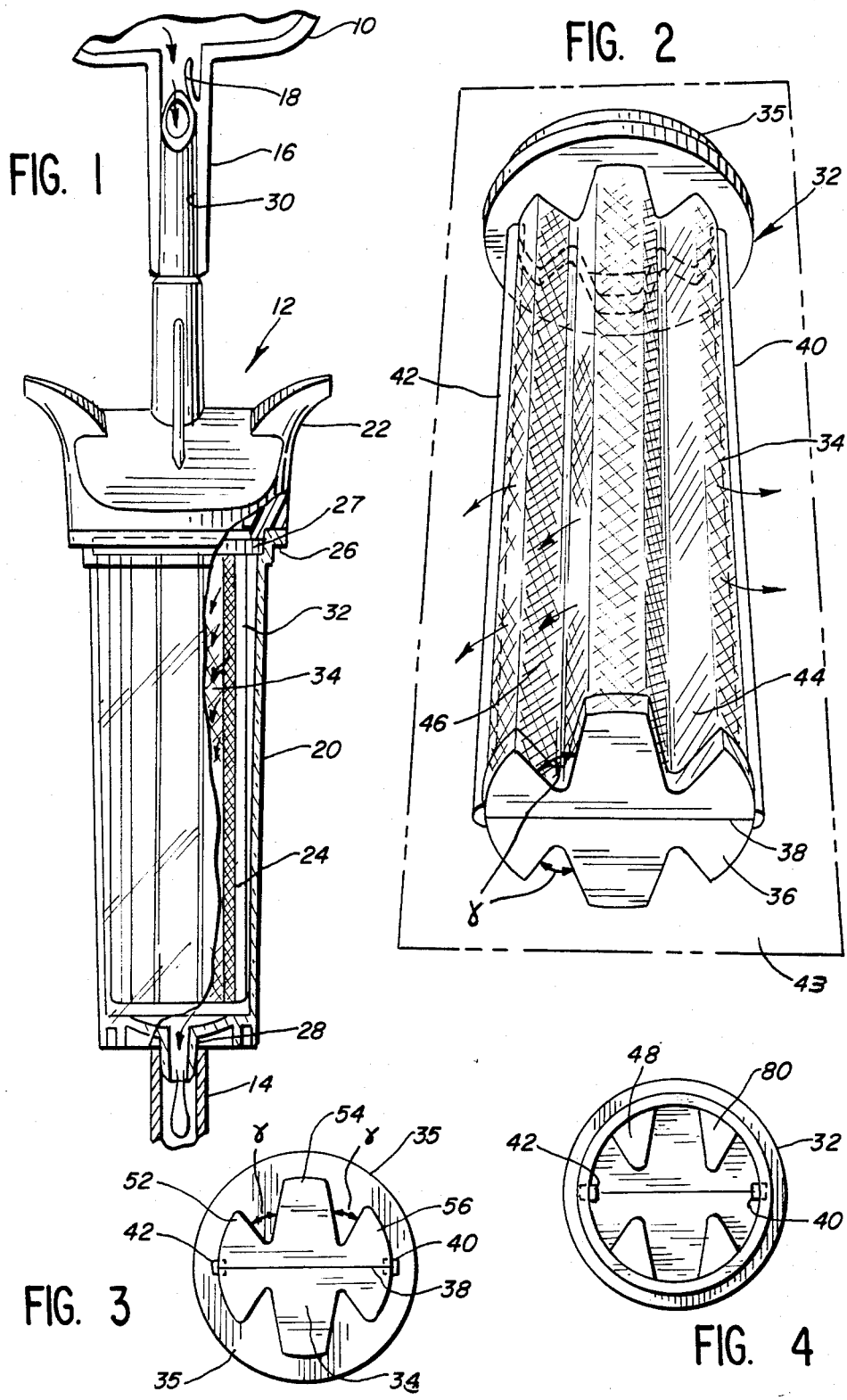

LOW VOLUME, LARGE AREA FILTERS FOR IV OR BLOOD FILTRATION

This is a continuation of application Ser. No. 363,632, filed Mar. 30, 1982, now abandoned.

BACKGROUND OF THE INVENTION

There is disclosed herein a filter element, and in particular, a large surface area filter element for use in medical applications.

In many medical applications fluids, such as blood, intravenous solutions, etc., are filtered to remove undesirable filtratable constituents. In some applications, such as flood filtration, surface-type or depth-type filter media is used. Surface-type media is usually a web of open-mesh material which is held, by a frame, in a filtering position. Depth-type media is usually a pad of fibrous or porous material.

In blood administration sets, blood or plasma is conducted from a reservoir, usually a flexible plastic bag, through a drip chamber and then to the patient via a catheter. Such sets are sold by Travenol Laboratories, Inc., Deerfield, Ill., under product code numbers such as 2C2037 and 2C2157.

The drip chamber may include a filter element so that blood entering the chamber flows through the filter element and then exits the chamber. The drip chamber controls the delivery of fluid on a drop-by-drop basis.

In some constructions, the drip chamber includes a cylindrical housing, a cylindrical filter element that fits into the housing, and a cap that seals the chamber. The filter element includes an injection molded frame and a surface-type or depth-type filter media supported by the frame. The filter media has a generally cylindrical surface. The molding technique employs a split mold cavity and core which permits injection molding of the frame and attachment of the filter media in one step. This is sometimes referred to as overmolding.

It has been determined that in some applications, it is desirable to increase the filtering ability of the filter. However, it may be undesirable to increase the length or width of the filter as that would require changing the geometry (i.e., size and shape) of the drip chamber.

Pleating of a filter can increase the surface area, but pleated filters have not been made using molding techniques as pleated filters include undercuts or re-entrant angles that would preclude opening of the mold to remove the filter element without destruction of the element.

It is therefore an object of this invention to increase the filtering capacity of a medical filter element without changing the size and shape of the related housing.

It is another object of this invention to increase the filtering capacity of a medical filter element while still permitting the filter element to be manufactured by molding.

These and other objects of this invention will become apparent from the following description and appended claims.

SUMMARY OF THE INVENTION

There is disclosed herein a filter element which has been adapted for use in existing housings, but which is of greater filtering capacity than prior filters, but of the same physical size. The filter media is of the surface-type or depth-type and is pleated so as to provide greater surface area. The filter element is manufactured by injection molding the frame to the media. The frame is molded and includes a parting line that lies in the plane which includes the body's longitudinal axis.

The filter frame includes pleat-forming projections and shoulders which cooperate in forming pleats in the surface media. The pleats are formed such that the pleat-forming surfaces open away from the parting-line plane. In other words, the pleats do not include the undercuts or re-entrant angles relative to the parting-line plane. Thus the mold cavity can open and release from the filter element. This construction and method of molding provide ease of fabrication and a high filtration surface area filter element.

BRIEF DESCRIPTION OF THE DRAWINGS

FIG. 1 is an elevational view showing a partially broken away drip chamber with a filter element in place;

FIG. 2 is a perspective view of a greatly enlarged pleated filter element;

FIG. 3 is an elevational view of the bottom or terminal end of the filter element;

FIG. 4 is an elevational view of the top or inlet end of the filter element;

DESCRIPTION OF THE PREFERRED EMBODIMENT

Figure 5:
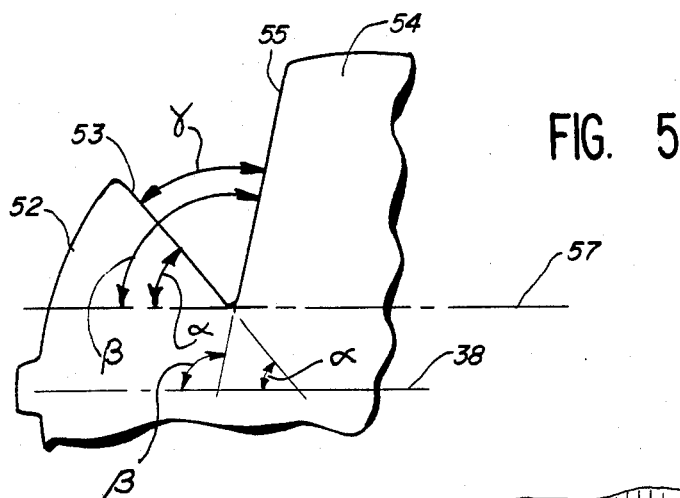
FIG. 5 is a greatly enlarged view of one section of the end plate showing the angular relationships for the pleat-forming surfaces.
Figure 6:
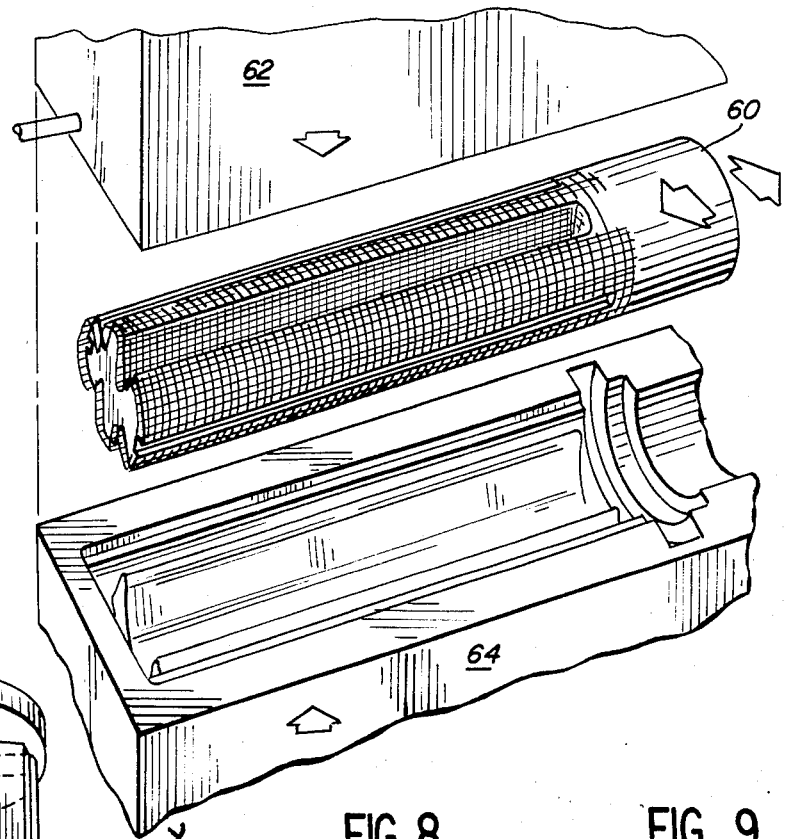
FIG. 6 is a diagrammatic view showing the mold cavities and core for forming a pleated filter element.

Referring now to the drawings, there is shown, in FIG. 1, a blood plasma reservoir 10, a drip chamber assembly 12, and catheter tubing 14. The bag 10 includes an outlet tube 16 having a pierceable membrane seal 18.

The drip chamber 12 includes a cylindrical housing or body 20, a cap-and-spike assembly 22, and a filter element 24. The housing 20 has an open top 26 which has a stepped shoulder 27 for supporting the filter 24 and a drop outlet 28 at the bottom or terminal end. The cap 22 is sealed to the top 26 of the housing 20 and has a fluid conducting spike 30 for insertion into the outlet tube 16 and for puncturing the seal 18. The spike thus provides the inlet by which blood or other liquids can flow from the bag 10 to the filter 24. The filter element includes a support frame 32 and the filter media 34.

In operation, blood exiting the bag 10 flows into the chamber spike 30 and downwardly into the drip chamber body 20. The blood enters the top of the filter element 24 and then flows outwardly through the filter media and downwardly to the bottom of the body 20. The blood exits the housing 20 through the outlet 28 which is connected to the catheter tubing 14.

The filter element 24 is best seen in FIG. 2. The frame 32 includes an upper ring-like inlet end 35, a flat, fluid-impervious terminal end plate 36 on which the parting line 38 can be seen and a pair of interconnecting side ribs 40 and 42. A parting line plane 43 passes through the element along the mold parting line and the longitudinal axis of the body lies in the parting line plane.

The filter element is symmetrical with respect to the parting line plane. The surface filter media 34 is bonded to the frame and includes pleats such as 44 and 46. The pleats are formed during molding and are shaped in cooperation with internal projections such as 48 and 50 on the inlet end 35 and external groove forming shoulders such as 52, 54 and 56 on the terminal end 36.

The pleats are formed such that the pleat angle gamma ($\gamma$) opens outwardly from the parting line 38 so as to permit retraction of mold parts.

The pleat angle ($\gamma$) can be defined by its angular relations to the parting line. But it is more convenient to define the angles relative to a line 57 parallel to the parting line 38. The external shoulders 52, 54 and 56 define surfaces which in turn define grooves that are aligned with the pleats. For example, the shoulder 52 defines a first groove surface 53 and the shoulder 54 defines a second groove surface 55. The first surface 53 forms an acute angle alpha ($\alpha$) (i.e., less than 90 degrees) with the parting line plane, or the parallel line 57, and the second surface 55 forms an obtuse angle ($\beta$) (i.e., greater than 90 degrees) with the parting line plane, or parallel line 57. It can be seen that these angles can be measured at line 57 or by projections to the parting line. The second groove defined by shoulders 54 and 46 exhibits similar but mirror image relationships.

Turning now to FIG. 4, the surface of the inlet projections 48 and 50 also define the alpha ($\alpha$), beta ($\beta$), and gamma ($\gamma$) angular relationships as the terminal plate grooves. The alignment of the shoulders and grooves cooperate in forming the pleats of the filter media.

When using surface-type filter media, the filter element 24 is molded by providing a mold core 60 which has been shaped to provide the desired internal shape. A split mold cavity 62 and 64 is then provided which can surround the core and provide molding spaces between the core and closed cavity. The filter media 34 is then applied and positioned on the core, the cavity closed, and the frame forming plastic injected. The plastic bonds to the media, thus forming an integral part, and the heat sets the filter media to form the pleats.

Thereafter, the cavity is opened, the core is retracted and the molded element is ejected. This molding can take place because of the shape and positioning of the pleat grooves.

Figure 7:
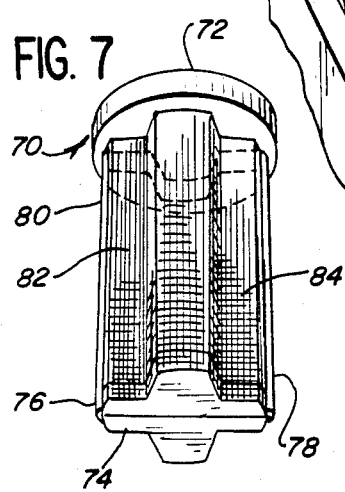
FIGS. 7, 8 and 9 are perspective and elevational views of another filter element configuration.
Figure 8:
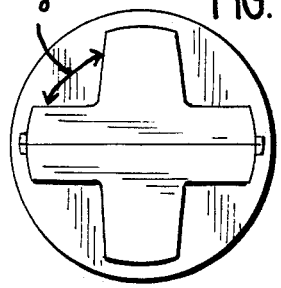
Figure 9:
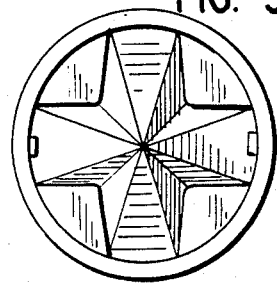

A small cross-shaped filter element is shown in FIGS. 7, 8 and 9. The filter element has a frame 70 which includes the inlet end 72, terminal plate 74 and ribs 76 and 78. The media 80 is overmolded to the frame 70 so as to form the cross-shape and pleats such as 82 and 84. Internal projections and grooves forming external shoulders are also provided. In FIG. 8, the pleat-forming angle gamma ($\gamma$) is shown. Alpha ($\alpha$) is about 0 degrees and beta ($\beta$) is about 90 degrees. Thus the pleat angle gamma ($\gamma$) is about equal to beta ($\beta$).

It will be appreciated that numerous changes and modifications can be made to the embodiment disclosed herein without departing from the spirit and scope of this invention.

What is claimed is:

1. A flow-through medical filter element which includes filter media means and frame-like means for supporting and positioning said filter media wherein:
   (a) said frame-like means is a molded member and includes a ring-like inlet end, a fluid-impervious terminal end spaced from said ring-like inlet, and a plurality of rib-like members which extend between and interconnect the inlet end and terminal end, said inlet end also having internally-extending pleat-supporting projections and said terminal end having complementary external pleat-supporting shoulders, said frame-like means being symmetrical about an axial plane which includes a mold parting line and said external shoulders being formed at angles which are not re-entrant with respect to said parting line and which permit separation of a mold along the parting line and release of the part; and
   (b) said filter media means having longitudinal pleats therein and said media being bonded to internal pleat-supporting projections at the inlet end and to the external pleat-supporting shoulders at the terminal end, whereby fluid enters the filter through the inlet, flows through the filter media and thereafter exits the filter element.

2. A filter element as in claim 1, whereby said terminal end shoulders form a plurality of groove-like shapes in said terminal end which open outwardly from said parting line.

3. A filter as in claim 2, wherein the angle ($\alpha$) between the parting line and a first groove-defining surface is acute and the angle ($\beta$) between the parting line and a second groove-defining surface is obtuse.

4. A filter as in claim 2, wherein the angle ($\alpha$) between the parting line and a first pleat surface is acute and the angle ($\beta$) between the parting line and a second pleat surface is obtuse.

5. A filter as in claim 4, wherein the pleat angle ($\gamma$) is equal to the difference between ($\beta$) and ($\alpha$).

6. A filter element as in claim 5, wherein said projections on the ring-like end are aligned with the groove-like members in said pleated surface media.

7. A filter element as in claim 6, wherein said filter element includes at least four pleats, with two pleats on each side of the parting line plane and wherein at least one pleat-forming surface for each pleat does not lie along a plane passing through the longitudinal axis of the filter element.

8. A filter element as in claim 7, wherein said element is symmetrical about a plane which includes the longitudinal axis of the element and which is transverse to the parting line plane.

9. A filter as in claim 1 wherein the angle-defining surfaces in the pleats in said filter media open away from the parting line so as to permit opening of the mold.

10. A filter as in claim 9, wherein the pleat angle in the terminal end plate equals and is aligned with the groove angle in said pleats.

11. A filter element as in claim 1, wherein said filter media is of the surface-type.

12. A filter element as in claim 1, wherein said filter media is of the depth-type.

13. A one-piece unitary medical filter element which includes pleated filter media and frame-like means for supporting and positioning said filter media wherein:
   (a) said frame-like means is an elongated, molded member and includes:
      a first end, a second end spaced from said first end, at least one of said ends defining a fluid flow aperture, and
      a plurality of rib-like members which extend between and interconnect said first end and second end, said first end having pleat-supporting means and said second end having cooperating pleat-supporting means,
      said frame-like means being symmetrical about a longitudinal and axial plane which includes a mold parting line, and each of said pleat-supporting means defining angles therebetween which are not re-entrant and are open relative to said parting line so as to permit opening of a mold along the mold-parting line, release of the part and cooperate in shaping the filter media pleats; and (b) said filter media having longitudinal pleats therein and said media being physically bonded to said pleat-supporting means so as to form a unitary filter element.

14. A filter element as in claim 13, wherein said first end includes means defining a fluid flow aperture therethrough; and said second end is impervious to fluid flow.

15. A filter element as in claim 14, wherein said aperture in said first end defines a fluid inlet through which fluid to be filtered enters said filter element and wherein fluid is filtered and exits said element through said pleated filter media.

16. A filter element as in claim 15, wherein:

said first end includes a ring-like structure which defines a fluid flow aperture and said pleat-supporting means includes a plurality of internally-extending pleat-supporting projections; and said second end pleat-supporting means includes a plurality of external pleat-supporting shoulders which are complementary in shape to said pleat-supporting projections;

whereby said internal pleat-supporting projections and external pleat-supporting shoulders cooperate in shaping the pleated filter media.

17. A process for molding a flow-through medical filter element which includes integral pleated filter media means and frame-like means for supporting and positioning the media means, said process comprising the steps of:

providing a mold having an elongated shaped mold core and a complementary shaped split mold cavity for surrounding said core and defining a mold space between the core and cavity, said mold cavity defining a longitudinal parting line plane and said core having a plurality of pleat-forming grooves therein, each of which open away from the parting line so as to form open angles relative to said mold cavity;

applying filter media to said core and in said core grooves;

closing said mold cavity sections about said core;

injecting plastic into the mold cavity space so as to form the frame-like means and bond the same to the filter media;

separating said mold cavity from said mold core by separating said mold cavity pieces relative to parting line plane; and removing said filter element from said core by sliding said element from said core.

* * * * *